(12) United States Patent
McGahan et al.

(10) Patent No.: US 12,076,105 B2
(45) Date of Patent: Sep. 3, 2024

(54) SURGICAL DRAPING SYSTEM AND METHOD

(71) Applicant: WARSAW ORTHOPEDIC INC., Warsaw, IN (US)

(72) Inventors: Thomas V. McGahan, Germantown, TN (US); Roy K. Lim, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 635 days.

(21) Appl. No.: 17/308,319

(22) Filed: May 5, 2021

(65) Prior Publication Data

US 2021/0267706 A1    Sep. 2, 2021

Related U.S. Application Data

(63) Continuation of application No. 15/480,170, filed on Apr. 5, 2017, now Pat. No. 11,051,899.

(51) Int. Cl.
| | | |
|---|---|---|
| *A61B 46/00* | (2016.01) | |
| *A61B 46/20* | (2016.01) | |
| *A61B 46/27* | (2016.01) | |
| *A61B 17/00* | (2006.01) | |

(52) U.S. Cl.
CPC .............. *A61B 46/27* (2016.02); *A61B 46/00* (2016.02); *A61B 46/20* (2016.02); *A61B 46/40* (2016.02); *A61B 2017/00946* (2013.01); *A61B 2046/205* (2016.02)

(58) Field of Classification Search
CPC ......... A61B 46/00; A61B 46/10; A61B 46/13; A61B 46/20; A61B 46/27; A61B 46/30; A61B 46/40; A61B 2046/201; A61B 2046/205; A61B 2046/234; A61B 2017/00946

See application file for complete search history.

(56) References Cited

U.S. PATENT DOCUMENTS

| 4,350,246 A | 9/1982 | Mayer |
|---|---|---|
| 4,998,538 A | 3/1991 | Charowsky et al. |
| 5,417,225 A | 5/1995 | Rubenstein et al. |

(Continued)

FOREIGN PATENT DOCUMENTS

| CN | 104080419 A | 2/2017 |
|---|---|---|
| JP | 2012-517326 A | 3/2017 |

(Continued)

OTHER PUBLICATIONS

IP Australia—Australian Patent Office, Application No. 2018249836, Examination report No.2 for standard patent application, Date of this report: Mar. 10, 2023.

(Continued)

*Primary Examiner* — Keri J Nelson
(74) *Attorney, Agent, or Firm* — Sorell, Lenna & Schmidt, LLP

(57) ABSTRACT

A surgical drape includes a seal connectable with a selected surface of a body to define a sterile region that includes access to at least two surgical approaches. A sleeve is connected with the seal and a draping is disposed with the body. The sleeve defines a cavity in communication with the region. Surgical instruments, systems and methods are disclosed.

20 Claims, 5 Drawing Sheets

(56) References Cited

U.S. PATENT DOCUMENTS

| | | | |
|---|---|---|---|
| 5,433,221 | A | 7/1995 | Adair |
| 5,523,581 | A | 6/1996 | Cadwalader |
| 5,649,550 | A | 7/1997 | Crook |
| 5,676,159 | A | 10/1997 | Navis |
| 5,813,409 | A | 9/1998 | Leahy et al. |
| 6,278,125 | B1 | 8/2001 | Belek |
| 6,357,445 | B1 | 3/2002 | Shaw |
| 6,485,467 | B1 | 11/2002 | Crook et al. |
| 7,604,007 | B1 | 10/2009 | Wooley |
| 7,717,117 | B2 | 5/2010 | Duarte |
| 7,763,060 | B2 * | 7/2010 | Baumann ............ A61F 7/02 607/104 |
| 8,807,138 | B2 | 8/2014 | Byers et al. |
| 8,999,485 | B2 * | 4/2015 | Otomo ............ C08L 83/04 524/588 |
| 9,176,487 | B2 | 11/2015 | Sperling et al. |
| 11,051,899 | B2 * | 7/2021 | McGahan ............ A61B 46/40 |
| 2002/0109107 | A1 | 8/2002 | Goldstein |
| 2003/0192553 | A1 * | 10/2003 | Rambo ............ A61B 17/3431 128/850 |
| 2003/0205233 | A1 | 11/2003 | Aboul-Hosn et al. |
| 2013/0101653 | A1 | 4/2013 | Sperling et al. |
| 2013/0112211 | A1 | 5/2013 | Power et al. |
| 2014/0155791 | A1 * | 6/2014 | Robinson ............ A61M 1/915 601/7 |
| 2015/0342685 | A1 | 12/2015 | Livesey |
| 2016/0135915 | A1 | 5/2016 | Czajka, Jr. et al. |
| 2017/0325800 | A1 * | 11/2017 | Prior ............ A61B 17/00234 |

FOREIGN PATENT DOCUMENTS

| | | |
|---|---|---|
| WO | 1996038096 A1 | 12/1996 |
| WO | 2015117193 A1 | 8/2015 |
| WO | 2015191953 A1 | 12/2015 |

OTHER PUBLICATIONS

IP Australia—Australian Patent Office, Application number: 2018249836, Examination report No. 1 for standard patent application, Date of this report: Dec. 15, 2022.
CNIPA China National Intellectual Property Administration, Notice of the First Office Action, Date of Dispatch: Dec. 29, 2021 Application No. 201880017224.X, Applicant: Warsaw Orthopedic, Inc.
Korean Intellectual Property Office, Government Complex Daejeon Building 4, 189, Cheongsa-ro, Seo gu, Daejeon, 35208, Republic of Korea, Korean Patent Application No. 10-2019-7029584 corresponding to PCT/US2018/025985, Mailed May 23, 2022.
Patent Office, Office Action dated Sep. 17, 2021, Japanese Patent Appln. No. 2019-553284.

* cited by examiner

SURGICAL DRAPING SYSTEM AND METHOD

CROSS REFERENCE TO RELATED APPLICATIONS

This application is a continuation of U.S. patent application Ser. No. 15/480,170, filed Apr. 15, 2017, which is expressly incorporated by reference herein, in its entirety.

TECHNICAL FIELD

The present disclosure generally relates to medical devices for the treatment of musculoskeletal disorders, and more particularly to a surgical draping system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders can include correction, fusion, fixation, discectomy, laminectomy and implantable prosthetics. As part of these surgical treatments, spinal implants including spinal constructs and interbody devices are often used to restore proper alignment and generally support the vertebral members. During surgical treatment, a surgical procedure can employ a surgical drape that covers a patient positioned on a surgical table in an operating room to provide a sterile region. This disclosure describes an improvement over these prior technologies.

SUMMARY

In one embodiment, a surgical drape is provided. The surgical drape includes a seal connectable with a selected surface of a body to define a sterile region that includes access to at least two surgical approaches. A sleeve is connected with the seal and a draping is disposed with the body. The sleeve defines a cavity in communication with the region. In some embodiments, surgical instruments, systems and methods are disclosed.

In one embodiment, the surgical drape includes a gasket adherable to a selected surface of a body to define a sterile boundary. A movable sleeve is connected with the gasket and a draping is disposed with the body. The sleeve and the gasket define a region within the boundary that includes access to at least two surgical approaches to the body.

In one embodiment, a surgical system includes a sleeve including a gasket and being connectable with a selected surface of a body to define a sterile region that includes access to at least two surgical approaches. The sleeve defines an inner cavity in communication with the region. An over drape defines an opening configured for disposal of the sleeve.

BRIEF DESCRIPTION OF THE DRAWINGS

The present disclosure will become more readily apparent from the specific description accompanied by the following drawings, in which.

DETAILED DESCRIPTION

Figure 1:
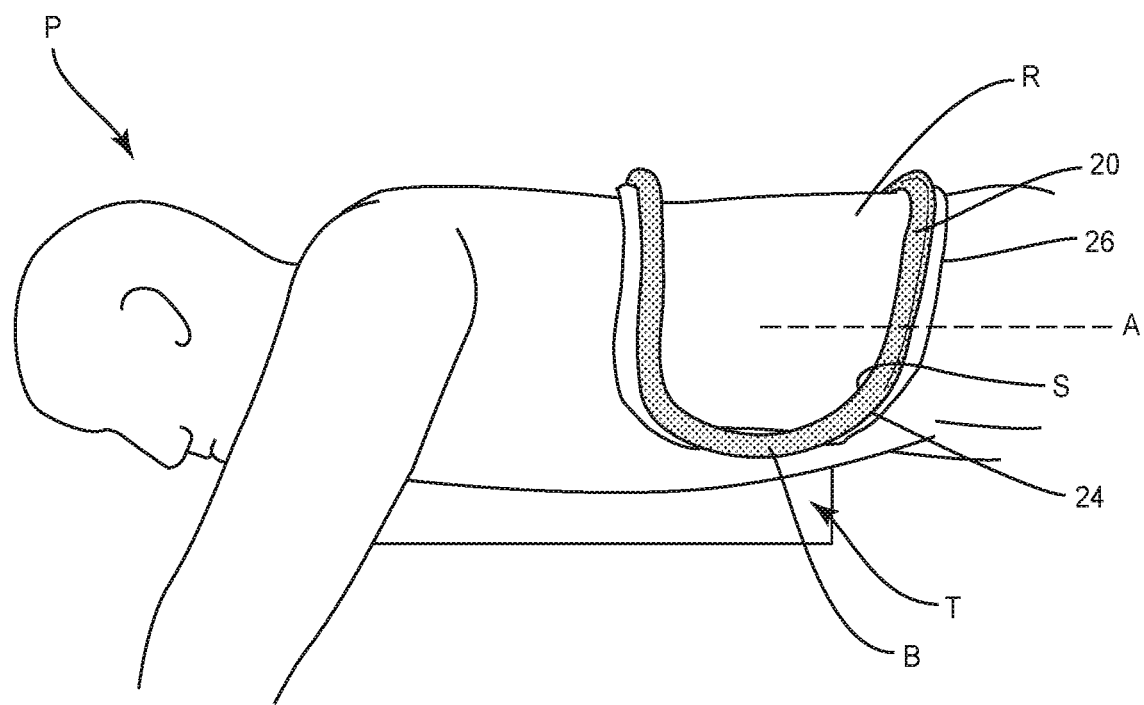
FIG. 1 is a perspective view of components of one embodiment of a surgical system in accordance with the principles of the present disclosure disposed with a patient body.

The exemplary embodiments of the surgical system and related methods of use disclosed are discussed in terms of medical devices for the treatment of musculoskeletal disorders and more particularly, in terms of a surgical draping system and method for treating a spine. In some embodiments, the systems and methods of the present disclosure comprise medical devices that establish and maintain a sterile surgical field with a patient and are employed with a surgical treatment of a cervical, thoracic, lumbar and/or sacral region of a spine. In some embodiments, the present disclosure includes a surgical draping system employed with a surgical table that can rotate a patient into alignment with one or more surgical approaches, as described herein, while establishing and maintaining a sterile surgical field.

In some embodiments, the present system comprises a surgical drape for angular rotation of a patient during spine surgery. In some embodiments, the present system comprises a surgical drape including a sterile oval configuration sized to define one or a plurality of surgical approaches, such as, for example, a prone surgical access and a lateral surgical access. In some embodiments, the surgical drape is adhered to a patient during an initial preparation of a sterile surgical site.

In some embodiments, the present system includes a flexible tube that is attached to the surgical drape and is drawn through an oval cutout in a single over drape. In some embodiments, the tube is adhered to a top surface of the over drape. In some embodiments, this configuration allows a patient to be rotated 90 angular degrees below the over drape while maintaining sterility within an oval tube. In some embodiments, this configuration allows a patient to be rotated through an angular range of 0 through 180 degrees below the over drape while maintaining sterility within an oval tube. In some embodiments, this configuration allows for the use of a single over and/or upper drape.

In some embodiments, the surgical drape and the flexible tube are applied to a patient while elevated in a sterile region above a beltline of a practitioner. In some embodiments, this approach confines sterile access to an area within the surgical drape and the flexible tube. In some embodiments, the surgical drape includes a flexible material that is adhered to a patient followed by attachment of a flexible tube to the surgical drape. In some embodiments, the surgical drape can be an integral part of the flexible tube attached to the patient.

In some embodiments, the surgical drape can be fabricated from various materials, as described herein.

In some embodiments, the present system comprises a surgical drape that provides the ability to define and isolate a sterile region during an initial patient preparation. In some embodiments, the surgical drape maintains sterility within an enclosed surgical field during angular rotation of a patient. In some embodiments, the surgical drape allows a 90 degree rotation of a patient positioned under a main drape. In some embodiments, the surgical drape contains a surgical site within a selected boundary defined by the tube.

In some embodiments, the present surgical draping system maintains a sterile surgical field with a patient during articulation of a patient. In some embodiments, the present surgical draping system maintains a sterile surgical field with a patient to provide simultaneous access to a plurality of surgical pathways and/or approaches, as described herein and for example, a posterior portion of a patient and a lateral portion of the patient accessed during one or more spinal procedures. In some embodiments, the present surgical draping system maintains a sterile surgical field with a patient to provide simultaneous access to an anterior portion of the patient and a lateral portion of the patient accessed during one or more spinal procedures. In some embodiments, the present surgical draping system provides simultaneous access to a plurality of surgical pathways and/or approaches in connection with simultaneous access to vertebral tissue at a surgical site via the plurality of surgical pathways and/or approaches. In some embodiments, the present surgical draping system provides simultaneous access to a plurality of surgical pathways and/or approaches in connection with sequential access to vertebral tissue at a surgical site.

In some embodiments, the present surgical draping system is employed with a method for treating a spine that includes the step of disposing an incise drape over a surgical site. In some embodiments, the incise drape may include a layer, substrate, film, sheet or covering disposed on or about the skin of a patient adjacent to the surgical site. In some embodiments, the incise drape includes a transparent, adhesive polyurethane film. In some embodiments, the present surgical draping system includes an antimicrobial incise drape with an iodophor impregnated adhesive that provides a sterile surface. In some embodiments, the present surgical draping system includes one or more surgical drapes applied superior and inferior to the incise drape.

In some embodiments, the present surgical draping system and method include applying the incise drape and one or more surgical drapes to the patient such that the incise drape and one or more surgical drapes remain flat on the patient. In some embodiments, the present surgical draping system and method include attaching a gasket of an access drape, as described herein, with adhesive directly to the incise drape. In some embodiments, the present surgical draping system and method include suspending an upper drape having an oval cut-out over the patient and attaching the upper drape to an open end of the access drape. In some embodiments, the upper drape is connected to drape poles at a head and a foot of the patient. As such, the upper drape remains relatively stationary. In some embodiments, the present surgical draping system and method include making a surgical incision through the access drape. In some embodiments, the present surgical draping system and method includes rotating the patient in a range of 0 through 90 angular degrees, independently, below the upper drape. In some embodiments, this configuration allows the surgeon access, which may include sequential access, to one or more surgical approaches, as described herein, independently and/or simultaneous access to one or more surgical approaches for one or more surgeons. In some embodiments, this configuration avoids the risks associated with a beltline designation of the sterile field during rotation of the patient below the upper drape.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone, lateral or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and iliac regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system and related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a surgical draping system 10.

The components of surgical draping system 10 can be fabricated from biologically acceptable materials suitable for medical applications. For example, the components of surgical draping system 10, individually or collectively, can be fabricated from materials such as super-elastic titanium alloys, superelastic metallic alloys (e.g., Nitinol, super elasto-plastic metals, such as GUM METAL®), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene or epoxy.

Various components of surgical draping system 10 may have material composites, including the above materials, to achieve various desired characteristics such as strength, rigidity, elasticity, compliance, biomechanical performance, durability and radiolucency or imaging preference. The components of surgical draping system 10, individually or collectively, may also be fabricated from a heterogeneous material such as a combination of two or more of the above-described materials. The components of surgical draping system 10 may be monolithically formed, integrally connected or include fastening elements and/or instruments, as described herein.

Surgical draping system 10 may be employed, for example, with minimally invasive procedures, including percutaneous techniques, mini-open surgical techniques and/or open surgical techniques to establish and maintain a sterile surgical field with a patient in connection with a surgical treatment of a spine. In some embodiments, the components of surgical draping system 10 are employed in connection with surgical treatment that includes access to a surgical site by one or a plurality of surgical approaches. For example, the components of surgical draping system 10 can be employed with spinal procedures that include access during a single procedure and/or simultaneous access to one or a plurality of surgical approaches and/or surgical pathways including one or more incisions within a sterile boundary. In some embodiments, during a surgical procedure, a patient is disposed with a surgical table that can articulate, orient, position, reposition and/or manipulate the patient for alignment with one or a plurality of surgical approaches. The components of surgical draping system 10 maintain sterility during such movement of the patient within an enclosed surgical field and/or boundary, for example, during angular rotation of a patient for alignment with one or a plurality of surgical approaches, as described herein. The surgical procedure can include surgical treatment of a cervical, thoracic, lumbar and/or sacral region of a spine.

Surgical draping system 10 includes an access drape 12. Drape 12 includes a seal, such as, for example, a gasket 20 and a sleeve 30 connectable with gasket 20, as described herein. Gasket 20 is configured to seal a space between an over and/or upper drape 60 and a surface S of a body of a patient P. Gasket 20 and sleeve 30 define a sterile boundary B around a sterile region R, as described herein.

Figure 2:
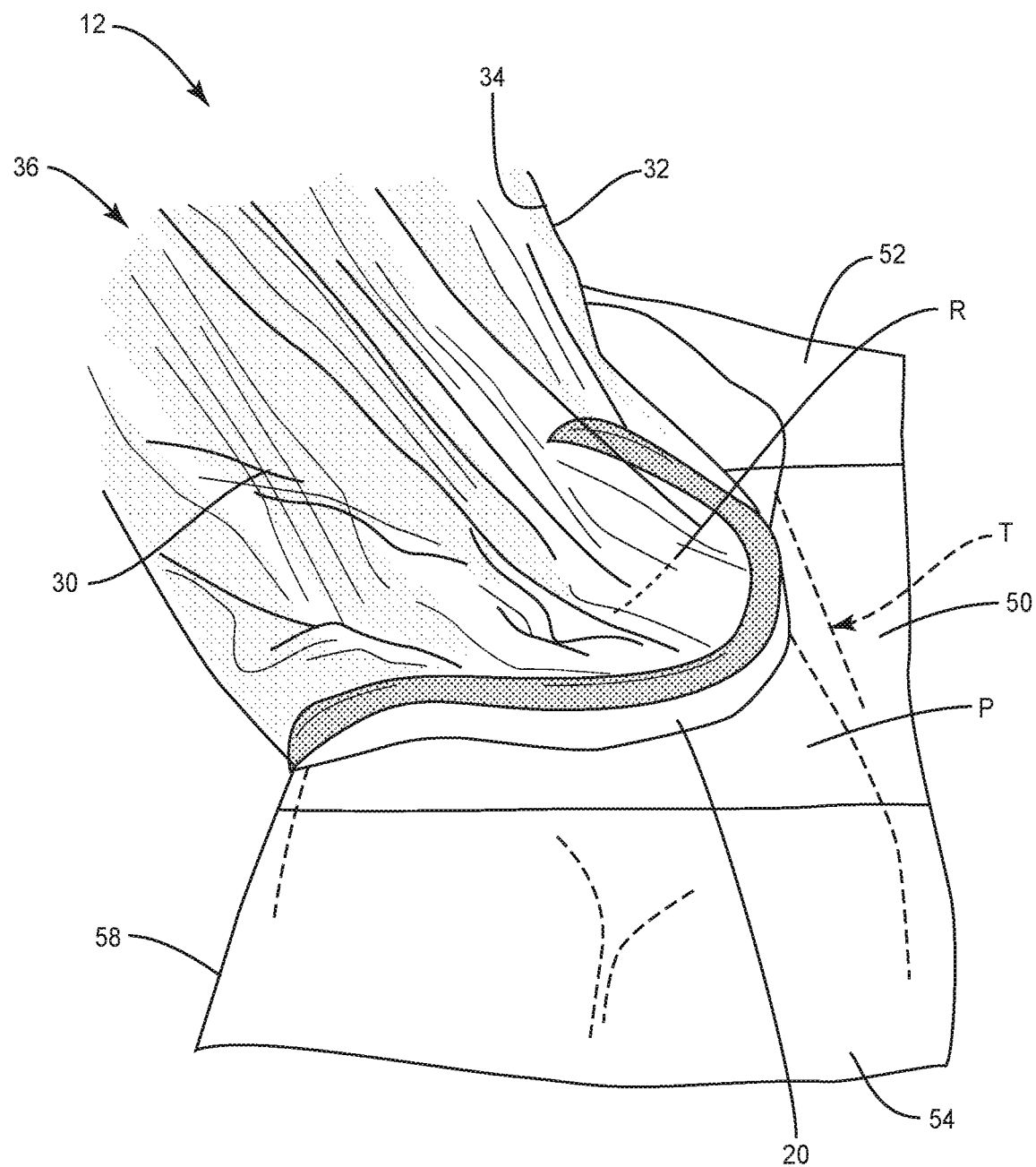
FIG. 2 is a perspective view of components of one embodiment of a surgical system in accordance with the principles of the present disclosure disposed with a patient body.
Figure 3:
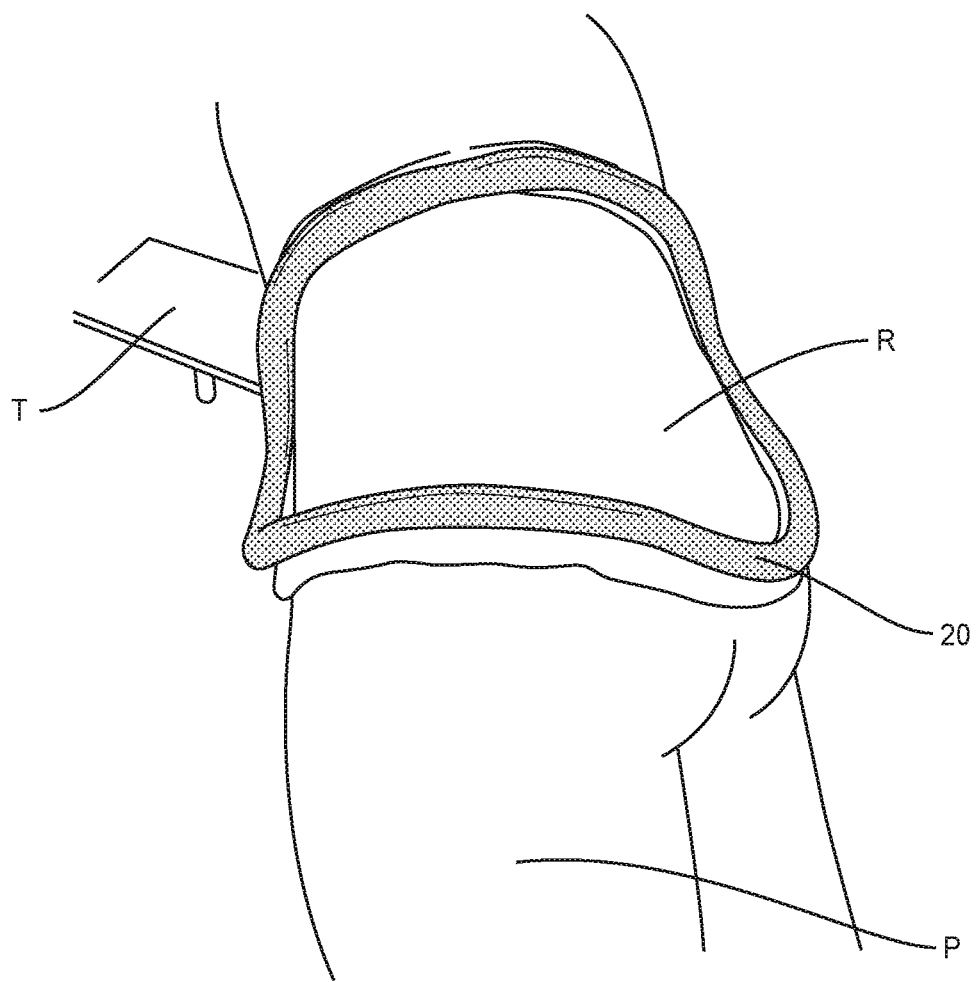
FIG. 3 is a perspective view of components of one embodiment of a surgical system in accordance with the principles of the present disclosure disposed with a patient body.

Gasket 20 includes a flexible configuration such that gasket 20 is malleable to a selected configuration for disposal about sterile region R. Sterile boundary B facilitates alignment and/or access via sleeve 30 to one or more surgical approaches, as described herein. In some embodiments, gasket 20 includes a surface 24 configured for direct engagement with surface S of patient P. In some embodiments, gasket 20 is adhered to an antimicrobial incise drape 50, as shown in FIG. 2, disposed on or about the skin of patient P. In some embodiments, surface 24 includes a planar configuration to facilitate engagement with surface S. In some embodiments, surface 24 is coated with a substrate 26. In some embodiments, substrate 26 is applied as an adhesive strip. In some embodiments, substrate 26 includes a pressure-sensitive material that facilitates adherence when applied to surface S. In some embodiments, gasket 20 is directly adhered to the skin of patient P.

In some embodiment, substrate 26 includes a bio-compatible, acrylic adhesive. In some embodiments, substrate 26 includes a soft acrylate adhesive or a silicone gel adhesive. In some embodiments, substrate 26 can be stretchable to facilitate manipulation of gasket 20 into a selected configuration. In some embodiments, substrate 26 includes a covering, such as, for example, a peel off layer to facilitate maintaining a sterile surface 24. In some embodiments, substrate 26 is configured to be removed from the skin of patient P without damage thereto and without causing pain.

Gasket 20 is connected and/or adhered to surface S during an initial preparation of a sterile surgical site. For example, substrate 26 is configured to fix gasket 20 to surface S such that substrate 26 is configured to resist and/or prevent disengagement of gasket 20 from surface S during rotation of patient P. Adherence of gasket 20 with surface S allows gasket 20 to rotate with the body of patient P as table T is rotated. Attachment of gasket 20 with surface S allows surgical drape system 10 to maintain sterile region R and/or sterile boundary B during rotation of patient P, as described herein. Rotation of the body of patient P provides access to one or more surgical approaches.

In some embodiments, the selected configuration of gasket 20 disposed with patient P is configured to provide access to one or more incisions disposed within sterile region R. In some embodiments, the selected configuration includes an oval. In some embodiments, the selected configuration may be manipulated to various geometry, such as, for example, polygonal, rectangular, square, circular or elliptical.

In some embodiments, gasket 20 can be fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and/or elastomeric composites. In some embodiments, gasket 20 may have a semi-rigid, rigid or elastic configuration, and/or have elastic properties, such as the elastic properties corresponding to the material examples described above. In some embodiments, gasket 20 may be fabricated from elastomeric materials such as, for example, Mylar, rubber, polyurethane, vinyl, latex, polyethylenes, ionomer, and PET, as well as less flexible materials such as stainless steel, titanium, nickel-titanium alloy, and ceramic mesh or weaved materials and combinations thereof.

Surgical drape system 10 includes sleeve 30 that defines a wall 32. Wall 32 includes an inner surface 34 that defines a cavity, such as, for example, a surgical pathway 36. Surgical pathway 36 is in communication with sterile region R and provides access to one or more incisions disposed within sterile region R. In some embodiments, sleeve 30 includes a tubular configuration and is movable and/or flexible in a plurality of orientations. Sleeve 30 extends from gasket 20 and is relatively movable in a plurality of orientations relative to gasket 20 to maintain sterile region R and/or sterile boundary B and provide access to one or more incisions disposed within sterile region R corresponding to and/or in alignment with one or more surgical approaches.

In some embodiments, sleeve 30 and gasket 20 are monolithically formed. In some embodiments, sleeve 30 is a separate component from gasket 20. In some embodiments, sleeve 30 is an integral component with gasket 20. In some embodiments, sleeve 30 is connected with gasket 20, such as, for example, with clips, hooks, adhesives and/or flanges. In some embodiments, gasket 20 is disposed around sterile region R so that drape 12 can provide sterile boundary B during simultaneous or sequential access procedures requiring simultaneous access to one or more surgical approaches.

For example, a surgeon formulates a surgical approach strategy for a surgical procedure to treat one or more spinal disorders. In some embodiments, the surgical procedure includes, but is not limited to, surgical treatment of a cervical, thoracic, lumbar and/or sacral region of a spine that may utilize access to a surgical site via one or more surgical approaches. The surgeon can employ drape 12 in connection with such access, which may include disposing a patient on surgical table T and articulating, orienting, positioning, repositioning and/or manipulating the patient for alignment with the surgical approaches. In some embodiments, the surgeon defines sterile region R by determining the selected surgical approaches, which may include one or more of anterior, posterior, posterior mid-line, direct lateral, postero-lateral, antero-lateral approaches and/or combinations thereof.

Gasket 20 is disposed around sterile region R so that drape 12 can provide sterile boundary B. Sterile boundary B encloses one or more incisions and/or openings of the selected surgical approaches. Sterile boundary B defines an enclosed surgical field that isolates sterile region R of patient P during the procedure and at the selected approaches. The components of surgical draping system 10 maintain sterility within sterile boundary B during rotation of patient P, as described herein.

In assembly, operation and use, as shown in FIGS. 1-5, surgical drape system 10, similar to the systems and methods described herein, includes access drape 12, which is employed in connection with a surgical approach strategy for a surgical procedure to treat one or more spinal disorders. In some embodiments, the components of surgical drape system 10 including drape 12 are employed with a lateral lumbar interbody graft/cage insertion with posterior instrumentation or constructs.

In connection with the procedure, a surgeon formulates a strategy for surgical treatment including access to a surgical site via one or more selected surgical approaches. For example, the lateral lumbar interbody graft insertion with posterior instrumentation can include access via a lateral surgical approach and a separate postero-lateral or posterior surgical approach. Drape 12 is connectable with upper drape 60, as described herein, to provide simultaneous access to the lateral and postero-lateral or posterior surgical approaches. Drape 12 maintains sterility of a surgical site during rotation, repositioning and/or manipulation of patient P, as described herein. In some embodiments, surgical access can include access and/or repositioning to a right lateral side portion, a left lateral side portion, an anterior portion and/or a posterior portion of patient P. In some embodiments, surgical access can include access to a posterior portion of a patient P and a lateral side of patient P. In some embodiments, surgical access can include access to an anterior portion of patient P and a lateral side of patient P.

Patient P is positioned on surgical table T in, for example, a prone position. Surgical table T is mechanically configured to rotate, reposition and/or manipulate patient P in connection with the spinal procedure to provide simultaneous access to the selected surgical approaches and/or vertebral tissue at the surgical site. In some embodiments, surgical table T rotates patient P into alignment with the selected surgical approaches via a 90 angular degree rotation of surgical table T about an axis A. In some embodiments, one or more practitioners may physically manipulate patient P for rotation to provide simultaneous access to the selected surgical approaches.

In connection with the selected surgical approaches, for example, the lateral and postero-lateral or posterior surgical approaches, the surgical site, which may include one or more incisions, retracted openings, pathways and/or passageways created with the body of patient P, are identified and/or determined to define sterile region R. For example, sterile region R includes the one or more incisions, retracted openings, pathways and/or passageways aligned with the lateral and postero-lateral or posterior surgical approaches created in the tissue surfaces of patient P disposed within selected tissue surface S, which bounds sterile region R. In some embodiments, sterile region R is established and maintained above a surface of surgical table T. In some embodiments, the space above the surface of surgical table T is considered a sterile region. In some embodiments, the space from surgical table T to the floor is considered a non-sterile region. In some embodiments, the surgical site and/or sterile region R include vertebral tissue.

In some embodiments, incise drape 50 is positioned over the surgical site and disposed on the skin of patient P, as shown in FIG. 2. A surgical drape 52 is applied to patient P in a superior orientation to incise drape 50 and a surgical drape 54 is applied to patient P in an inferior orientation to incise drape 50 to provide warmth to patient P. In some embodiments, incise drape 50 and drapes 52, 54 are applied and remain flat on patient P.

Gasket 20 is manipulated into a selected configuration for alignment and attachment with the surgical site. Gasket 20 is connected directly onto incise drape 50 and orientation with surface S of the body of patient P to define sterile region R about surface S, as described herein. Gasket 20 is adhered with incise drape 50 and connected with sleeve 30, as described herein, to define sterile boundary B. Sterile boundary B encloses the one or more incisions, retracted openings, pathways and/or passageways aligned with the lateral and postero-lateral or posterior surgical approaches created in the tissue surfaces of patient P to isolate sterile region R and provide simultaneous access to the selected surgical approaches during the surgical procedure.

Figure 5:
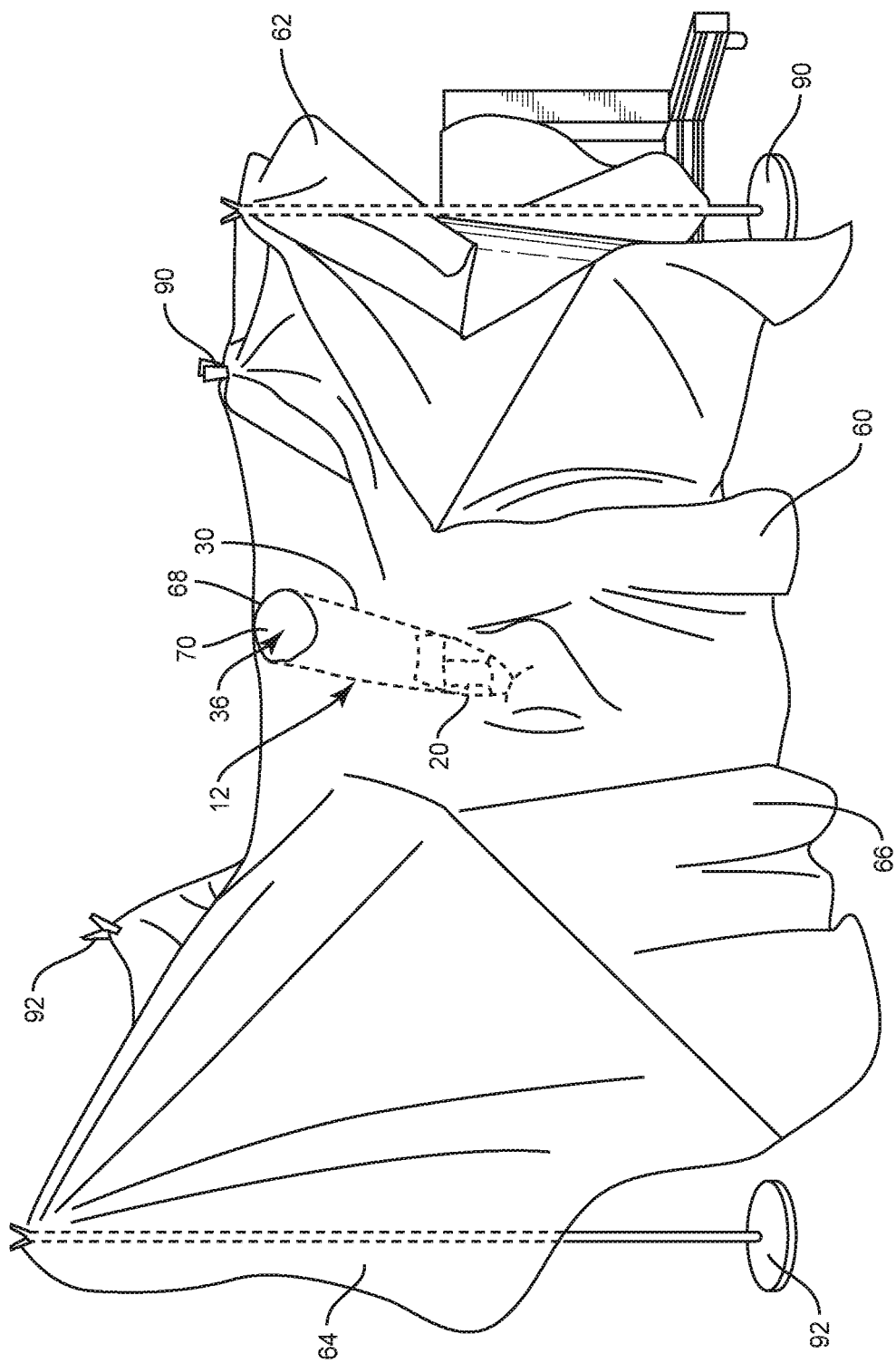
FIG. 5 is a perspective view of components of one embodiment of a surgical system in accordance with the principles of the present disclosure disposed with a patient body.

Upper drape 60 is connected with access drape 12. Upper drape 60 includes a cranial end 62, a caudal end 64 and a body portion 66. Upper drape 60 is configured to cover all or a portion of surgical table T and/or all or a portion of patient P. Ends 62, 64 are attached to drape poles 90, 92 at a head and a foot of patient P, and supported at a height above surgical table T and patient P, as shown in FIG. 5. In some embodiments, upper drape 60 is suspended and remains relatively stationary.

Upper drape 60 includes a surface 68 that defines an oval opening 70, which is suspended a distance over patient P. Surface 68 adjacent opening 70 is attached with surface 34 adjacent an open end of sleeve 30 for connecting upper drape 60 with access drape 12. Opening 70 is oriented for positioning relative to sterile region R and gasket 20. Opening 70 is in communication with surgical pathway 36 to provide access to one or more surgical approaches disposed within sterile region R during rotation of patient P using surgical table T, as described herein. In some embodiments, patient P can be rotated in a range of 0 through 90 angular degrees, for access to the one or more surgical approaches, below upper drape 60. This configuration allows the surgeon access to one or more surgical approaches, as described herein, independently and/or simultaneous access to one or more surgical approaches for one or more surgeons.

Figure 4:
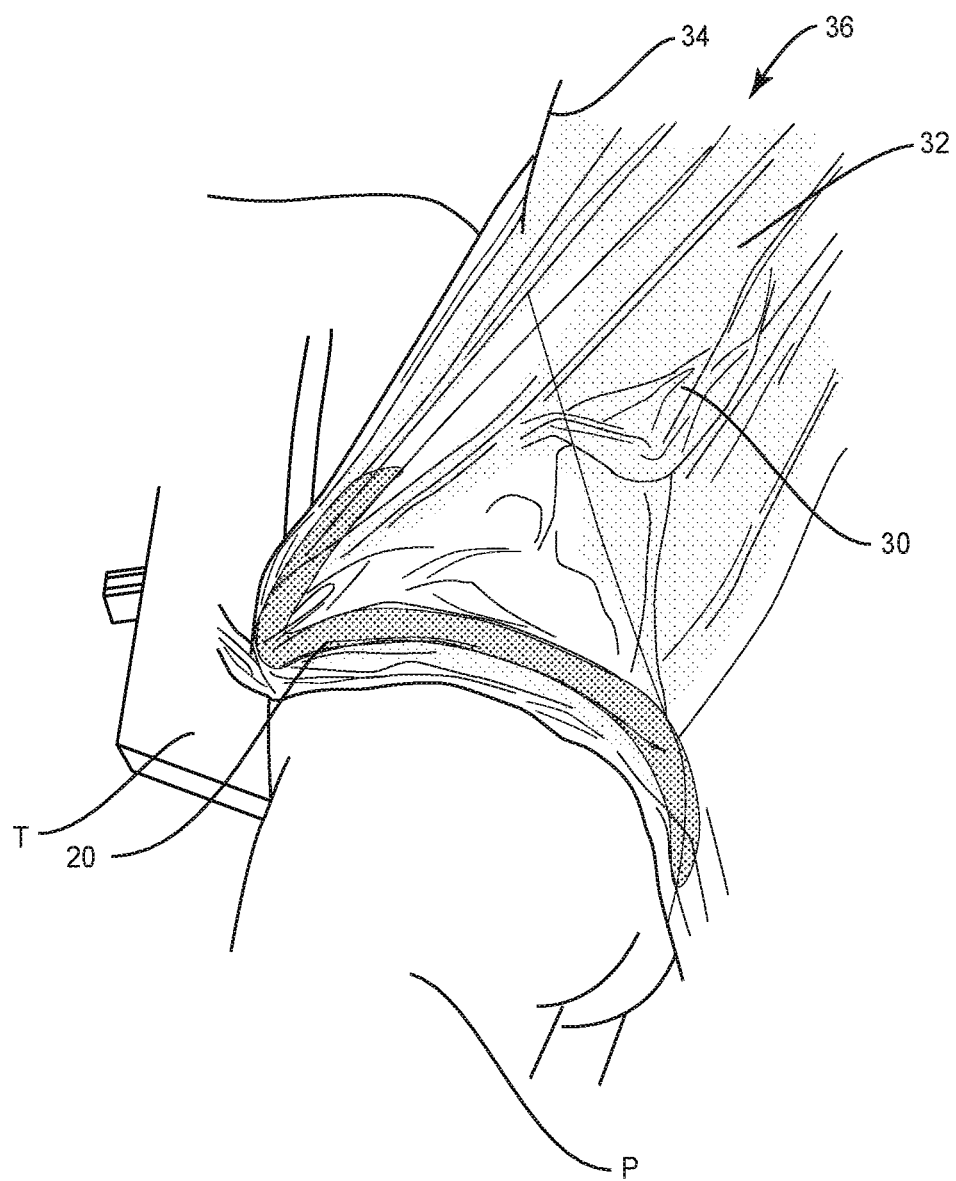
FIG. 4 is a perspective view of components of one embodiment of a surgical system in accordance with the principles of the present disclosure disposed with a patient body.

The surgeon can access surgical pathway 36 and the surgical site through opening 70 and access drape 12, and the surgical procedure is performed including making the one or more incisions, retracted openings, pathways and/or passageways in the tissue surfaces of patient P within sterile region R. In some embodiments, patient P is initially oriented in a lateral position or rotated by surgical table T from a prone position to a lateral position to provide surgical access via the lateral surgical approach to vertebral tissue within sterile region R, as shown in FIG. 4. A lateral lumbar interbody graft/cage insertion is performed via the lateral surgical approach. In some embodiments, patient P is initially oriented in a prone position or rotated by surgical table T from a lateral position to a prone position to provide surgical access via the postero-lateral or posterior surgical approaches to vertebral tissue within sterile region R, as shown in FIG. 2. Implantation of posterior instrumentation or constructs is performed via the postero-lateral or posterior surgical approaches. Sleeve 30 moves and/or articulates to adjust to the rotation of patient P and to provide simultaneous access to the selected surgical approaches. Movement of sleeve 30 and fixation and/or connection of gasket 20 with surface S creates sterile boundary B, which allows simultaneous access to the selected surgical approaches while maintaining sterile region R.

The lateral lumbar interbody graft insertion with posterior instrumentation utilizes drape 12 to establish and maintain sterile region R with sterile boundary B during rotation, repositioning and/or manipulation of patient P to provide simultaneous access to the selected surgical approaches. Upon completion of the procedure, the surgical instruments and non-implanted components are removed from the surgical site and the incisions, openings, pathways and/or passageways are closed. One or more of the components of surgical drape system 10 can be made of radiolucent materials such as polymers. Radiomarkers may be included for identification under x-ray, fluoroscopy, CT or other imaging techniques.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical drape comprising:
a sleeve extending along a vertical axis from a first end to an opposite second end, the sleeve having a length along the vertical axis;
a seal coupled to the first end, the seal including a gasket;
a first draping coupled directly to the second end, the first draping having a width along a horizontal axis, the horizontal axis extending transverse to the vertical axis, the width being greater than the length; and
a second draping coupled to the gasket.

2. The surgical drape recited in claim 1, wherein the length is defined by a distance from the first end to the second end.

3. The surgical drape recited in claim 1, wherein the width is defined by a distance from the second end to an outer perimeter of the first draping.

4. The surgical drape recited in claim 1, wherein the width is a maximum width of the first draping and the length is a maximum length of the sleeve.

5. The surgical drape recited in claim 1, wherein the sleeve consists of a tubular wall extending from the first end to the second end.

6. The surgical drape recited in claim 1, wherein an inner surface of the sleeve defines a cavity, the first end defining a first opening, the second end defining a second opening, the openings being in communication with the cavity, the second opening being coaxial with the first opening.

7. The surgical drape recited in claim 1, wherein an inner surface of the sleeve defines a cavity, the first end defining a first opening, the second end defining a second opening, the cavity being unobstructed from the first opening to the second opening.

8. The surgical drape recited in claim 1, wherein the seal is directly coupled to the first end.

9. The surgical drape recited in claim 1, wherein the seal is permanently coupled directly to the first end.

10. The surgical drape recited in claim 1, wherein the gasket is coated with a substrate, the substrate including a covering, the covering comprising a peel off layer.

11. The surgical drape recited in claim 1, wherein the sleeve and the seal are monolithically formed.

12. The surgical drape recited in claim 1, wherein the gasket is coated with a substrate, the substrate including a pressure-sensitive material that facilitates adherence.

13. The surgical drape recited in claim 1, wherein the seal includes liquid silicone rubber.

14. The surgical drape recited in claim 1, wherein the seal includes an adhesive strip.

15. The surgical drape recited in claim 1, wherein the seal includes an adhesive strip including a bio-compatible acrylic adhesive.

16. The surgical drape recited in claim 1, wherein the seal is malleable to a selected configuration.

17. The surgical drape recited in claim 16, wherein the selected configuration is an oval.

18. The surgical drape recited in claim 1, wherein the first draping is an over drape and the second draping is an antimicrobial incise drape.

19. A surgical drape comprising:
- a sleeve consisting of a tubular wall extending along a vertical axis from a first end to an opposite second end, the sleeve having a maximum length along the vertical axis;
- a seal permanently coupled directly to the first end, the seal including a gasket;
- a first draping permanently coupled directly to the second end, the first draping having a maximum width along a horizontal axis, the horizontal axis extending transverse to the vertical axis, the maximum width being greater than the maximum length; and
- a second draping coupled to the gasket.

20. A surgical drape comprising:
- a sleeve consisting of a tubular wall extending along a vertical axis from a first end to an opposite second end, the sleeve having a length along the vertical axis defined by a distance from the first end to the second end;
- a seal permanently coupled directly to the first end, the seal including a gasket; and
- a first draping permanently coupled directly to the second end, the first draping having a width along a horizontal axis defined by a distance from the second end to an outer perimeter of the draping, the horizontal axis extending transverse to the vertical axis, the width being greater than the length; and
- a second draping coupled to the gasket.

* * * * *